United States Patent [19]

Seare, Jr.

[11] Patent Number: 5,759,204
[45] Date of Patent: Jun. 2, 1998

[54] METHODS AND APPARATUS FOR ESTABLISHING A STABLE BODY POCKET

[76] Inventor: William J. Seare, Jr., 3190 E. Chula Vista Cir., Salt Lake City, Utah 84121

[21] Appl. No.: 789,597

[22] Filed: Jan. 24, 1997

Related U.S. Application Data

[63] Continuation of Ser. No. 324,440, Oct. 17, 1994, abandoned, which is a continuation-in-part of Ser. No. 960,004, Oct. 13, 1992, Pat. No. 5,356,429, which is a continuation of Ser. No. 701,021, May 16, 1991, abandoned.

[51] Int. Cl.$^6$ ..................................................... A61F 2/02
[52] U.S. Cl. ............................................ 623/11; 623/8
[58] Field of Search ........................ 623/1, 7, 8, 11, 623/12, 16, 66, 13; 606/215, 151, 213

[56] References Cited

U.S. PATENT DOCUMENTS

| | | | |
|---|---|---|---|
| 3,577,837 | 5/1971 | Bader, Jr. | 623/16 |
| 4,298,998 | 11/1981 | Nacify | 623/8 |
| 4,505,266 | 3/1985 | Yannas et al. | 623/15 |
| 4,585,458 | 4/1986 | Kurland | 623/18 |
| 4,597,763 | 7/1986 | Schweikhart | 623/8 |
| 4,676,795 | 6/1987 | Grundei | 623/8 |
| 4,685,447 | 8/1987 | Iversen et al. | 623/8 |
| 4,769,038 | 9/1988 | Bendavid et al. | 623/13 |
| 4,773,909 | 9/1988 | Chaglassian | 623/8 |
| 4,790,848 | 12/1988 | Cronin | 623/8 |
| 4,936,858 | 6/1990 | O'Keeffe | 623/8 |
| 4,994,084 | 2/1991 | Brennan | 623/11 |
| 5,011,494 | 4/1991 | Von Recum et al. | 623/11 |
| 5,033,481 | 7/1991 | Heyler, III | 623/11 |
| 5,141,581 | 8/1992 | Markham | 623/11 |
| 5,186,711 | 2/1993 | Epstein | 423/11 |
| 5,254,133 | 10/1993 | Seid | 606/215 |
| 5,376,117 | 12/1994 | Pinchuk et al. | 623/11 |
| 5,522,896 | 6/1996 | Prescott | 623/11 |

FOREIGN PATENT DOCUMENTS

| | | | |
|---|---|---|---|
| 3609910 | 10/1987 | Germany | 623/11 |

OTHER PUBLICATIONS

White, R.A., "*Replamineform: A New Process for Preparing Porous Ceramlic, Metal and Polymer Prosthetic Materials,*" (1972) pp. 922–924.

*Primary Examiner*—David Isabella
*Attorney, Agent, or Firm*—Workman, Nydegger & Seeley

[57] ABSTRACT

The methods and apparatus of the present invention permit a stable body pocket to be formed utilizing multiple biocompatible sheets or using only a single biocompatible sheet positioned to create either a potential space or actual space stable body pocket. The sheets have one surface which permits tissue ingrowth and thereby stably secures the sheet in the desired position. The other sheet surface is nonadhering such that adherence to a facing surface does not occur thereby creating a stable body pocket. In addition, a stable body pocket can be formed by using a biocompatible sheet or sheets having a surface that is selectively capable of permitting tissue ingrowth such that some portions of the surface grows into the surrounding tissue and other portions of the surface do not adhere to the surrounding tissue. In this manner, the stable body pocket apparatus has flexible surface portions. Stable body pocket access channels can also be formed according to the methods and apparatus of the present invention. Such access channels can provide stable means for communicating between the exterior of the body and a natural or created internal body pocket. A method for forming a stable body pocket utilizing fluid pressure introduced into the space where a body pocket is desired is also in accord with the present invention.

9 Claims, 7 Drawing Sheets

METHODS AND APPARATUS FOR ESTABLISHING A STABLE BODY POCKET

RELATED APPLICATIONS

This application is a continuation of U.S. application Ser. No. 08/324,440, filed Oct. 17, 1994, now abandoned, which is a continuation-in-part of Ser. No. 07/960,004, filed Oct. 13, 1992 which will issue as U.S. Pat. No. 5,356,429 on Oct. 18, 1994, incorporated herein by reference, which was a continuation of Ser. No. 07/701,021, filed May 16, 1991, now abandoned.

BACKGROUND OF THE INVENTION

1. The Field of the Invention

This invention relates to body pockets in which implants, devices, fluids, bioactive or other such materials are placed and, more particularly, to methods and apparatus for establishing such body pockets.

2. The Relevant Technology

It is well-known that implantation of a foreign material or substance, such as a prosthetic implant, between tissue surfaces within a body causes a reaction which generally results in a fibrous capsule forming around the foreign material or substance. When the foreign material or substance is introduced, portions of the surrounding tissue surfaces which contact each other heal together such that any space between the tissue and the material is obliterated. This has the effect of contracting the surrounding tissue about the foreign material. In addition, the portions of the tissue surfaces which contact the foreign material, such as a smooth-surfaced prosthetic implant or even most textured surfaced implants, undergo fibrous tissue growth, generally called a tissue or implant "capsule," at the tissue-implant interface. The tissue capsule also tends to contract. In addition to possible undesirable cosmetic effects, the contraction of the capsule around the foreign material may cause significant discomfort, distortion, loss of function, and pain. Once capsular contraction occurs, the preferred method of treatment is surgical removal. However, after reimplantation of an implant, another capsule will form and contract around the replacement implant as well. One example of a problem due to capsular contraction is observed in connection with breast implants. Capsular contraction associated with such implants results in the implanted breast having a hard feel, an unnatural transition from normal tissue to implanted tissue, and an unnatural spherical appearance. Various approaches to this problem have been taken but the results to date are less than completely satisfactory. See, e.g., U.S. Pat. No. 4,298,998 issued to Naficy, incorporated herein by reference, and the references cited therein.

It would be advantageous to provide methods and apparatus for establishing a body pocket which would be stable such that undesired tissue molding and contraction around implants, devices, fluids, or other bioactive prostheses does not occur. It would be advantageous to provide methods and apparatus for promoting tissue ingrowth at an apparatus surface which served to secure the apparatus in position and prevent subsequent tissue distortion, loss of function, and contracture of an established body pocket.

SUMMARY AND OBJECTS OF THE INVENTION

The problems caused by tissue distortion and contracture surrounding materials such as implants, devices, fluids, or other bioactive prostheses, substances or tissues are well known. It would be advantageous to provide methods and apparatus for establishing a stable body pocket such that either a potential space or an actual space is created within a body. The term "stable" as herein used refers to a body pocket which is not subject to undesired tissue adherence, healing, distortion, and contraction in response to the introduction of a substance, material, implant, device, or tissue into the body pocket. The terms "potential space" and "actual space" as herein used refer to a space created between facing surfaces. Included within the scope of these definitions is the space between tissue surfaces, a tissue surface and an apparatus surface; or two or more apparatus surfaces. With reference to a "potential space," it is desired that the facing surfaces do not adhere to each other even though the facing surfaces are substantially in direct contact with each other. In this manner, the potential space can accommodate the introduction of some material into the space. With reference to an "actual space," it is desired that the facing surfaces, either tissue surfaces, a tissue surface and an apparatus surface, or apparatus surfaces, or any combination of these, will not adhere to each other but the facing surfaces are substantially maintained apart from each other rather than in direct contact with each other. In this manner, the actual space accommodates some desired material within the space.

A stable body pocket within a body is useful in a variety of ways. For example, a stable body pocket provides a containment space for implanting a medical device, implant, fluids or other such material or tissue. Positioning an implant within a stable body pocket avoids problems caused by tissue adherence, distortion and contraction around implanted or transplanted objects. Transplanted tissue is advantageously positioned within a stable body pocket. Examples of medical devices include such things as an insulin infusion pump, dialysis catheters or various prosthetic implants, such as a breast implant. An artificial organ, such as an artificial heart or heart assist device, could be positioned within a stable body pocket. A stable body pocket could provide an internal compliance chamber to facilitate operation of an artificial heart or heart assist device within a body. In addition, a stable access channel in accord with the present invention could be brought out through the skin to provide the necessary accessing means for an implanted artificial heart to external drivers, monitors, or other components. Another use of such a stable access channel would be to provide access for continuous ambulatory peritoneal dialysis.

In view of the foregoing, it will be appreciated that it is an object of the present invention to provide methods and apparatus permitting a stable body pocket to be established such that either a potential space stable body pocket or an actual space stable body pocket is created within a body that can be utilized to position, house, and or otherwise facilitate the functioning of a material such as a medical implant, device, fluid, substance, or other such bioactive material, or tissue, therein.

It is another object of the present invention to provide methods and apparatus permitting a stable body pocket to be established such that either a potential space stable body pocket or an actual space stable body pocket is created and for permitting establishment of a stable access channel into a body pocket, or other potential space within the body, from outside of the body, or from a body pocket or potential space to another body pocket or potential space within the body.

The methods and apparatus of the present invention permit a stable body pocket to be formed utilizing multiple biocompatible sheets or using only a single biocompatible sheet positioned to create either a potential space or actual space stable body pocket. In addition, a stable body pocket can be formed by using a biocompatible sheet or sheets having a surface that is selectively capable of permitting tissue ingrowth such that some portions of the surface grows into the surrounding tissue and other portions of the surface do not adhere to the surrounding tissue. In this manner, the stable body pocket apparatus has flexible surface portions. Stable body pocket access channels can also be formed according to the methods and apparatus of the present invention. Such access channels can provide stable means for communicating between the exterior of the body and a natural or created internal body pocket. A method for forming a stable body pocket utilizing fluid pressure introduced into the space where a body pocket is desired is also in accord with the present invention.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

This invention relates to methods and apparatus for establishing a stable body pocket within a body such that either a potential space or an actual space is created. The term "stable" as herein used refers to a body pocket which is not subject to undesired tissue adherence, distortion and/or contraction in response to the introduction of material such as a substance, fluid, implant, device, tissue, or other bioactive prostheses into the body pocket. The terms "potential space" and "actual space" as herein used refer to a space created between two facing surfaces. Included within the scope of these definitions is the space between tissue surfaces; a tissue surface and an apparatus surface; apparatus surfaces; or any combination of these. With reference to a "potential space," it is desired that the facing surfaces not adhere to each other even though the facing surfaces are substantially in direct contact with each other. In this manner, the potential space can accommodate the introduction of some material such as a substance, fluid, implant, device, tissue, or other bioactive prostheses. With reference to an "actual space," it is desired that the facing surfaces, either tissue surfaces, a tissue surface and an apparatus surface, apparatus surfaces, or any combination of these wherein the facing surfaces also will not adhere to each other but the facing surfaces are substantially maintained apart from each other rather than in direct contact with each other. In this manner, the actual space accommodates a desired material therein. In addition, there may be combination of potential spaces and actual spaces created along any of the tissue surfaces.

A stable body pocket could be utilized in a variety of ways. For example, a stable body pocket can accept a medical implant, device or tissue therein without problems due to tissue adherence, distortion and/or contraction. Transplanted tissue could also be advantageously positioned within a stable body pocket. Examples of medical devices include such things as an insulin infusion pump or various prosthetic implants, such as a breast implant. An artificial organ, such as an artificial heart or heart assist device, could be positioned within a stable body pocket. A stable body pocket could provide an internal compliance chamber to facilitate operation of an artificial heart or heart assist device within a body. The stable body pocket compliance chamber would prevent the problem of changing the total compliance of the chamber over time due to the gradually increasing compliance from stiffening produced as the tissue encapsulation process progresses. Other potential uses for a stable body pocket include providing a space which could be filled with fluid, either liquid, gel or gas, or with a pharmaceutical composition, or with other materials, or substances such as, for example, silicone gel, or implants or devices such as breast implants or artificial hearts.

In addition, the stable body pocket could be made stably accessible from outside the body. An accessible body pocket could be utilized in numerous ways. For example, an accessible body pocket could provide means for performing continuous ambulatory peritoneal dialysis by allowing the direct insertion and removal of a catheter from the outside into the peritoneal cavity. Access to other such natural body pockets as well as from the outside to a created body pocket or access between either natural or created body pockets could also be stably maintained in accord with the present invention. Another example would be accommodation of an artificial heart or heart assist device and the necessary means for external access to the driver, for venting, or monitoring or other accessory components.

The present invention encompasses various methods and apparatus for establishing and maintaining a stable body pocket within a body. In addition, the present invention comprises methods and apparatus for permitting stable percutaneous access to a stable body pocket. Much of the following discussion is specifically directed to establishing and maintaining a stable body pocket for use with a breast implant. It is to be understood, however, that this is merely an illustrative use of the present invention. One of ordinary skill in the art will appreciate the applicability of the specific teachings of the present invention presented herein in any situation wherein it is useful to establish and maintain a stable body pocket.

1. Methods and Apparatus for Establishing a Stable Body Pocket Utilizing Multiple Elastomeric Sheets A preferred method and apparatus for establishing a stable body pocket utilizes multiple sheets, composed of a biocompatible material, each having one surface capable of promoting tissue ingrowth when placed in contact with surrounding tissue. The biocompatible material can be an elastomeric material or some other type. The other side of the biocompatible sheets has either a smooth or other type of non-adhering surface such that it does not adhere to other surfaces contacted. The sheets can be positioned within a space, either naturally occurring or surgically created, between facing tissue surfaces at a desired location within a body. If desired, the sheets may be stitched or otherwise secured into position. It should be understood, however, that the sheets become stably secured into position through the process of tissue ingrowth into the sheet surfaces.

Figure 1:
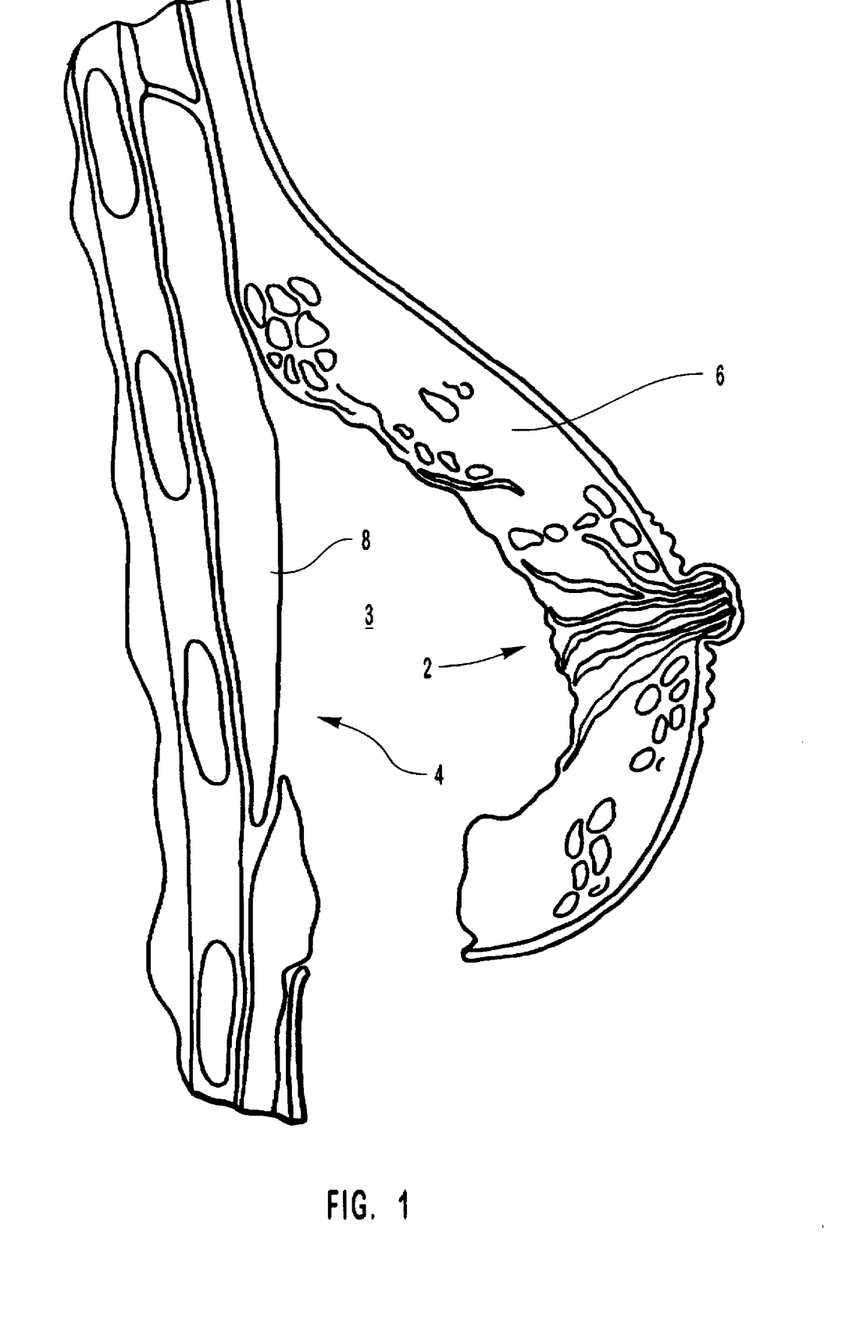
FIG. 1 illustrates an internal cross-section view of a space surgically created between tissue surfaces.

For example, as illustrated in FIG. 1, a space could be surgically created between tissue surfaces, designated 2 and 4, within the anterior chest. The tissue surface 2 is the under-surface of the breast gland 6. The tissue surface 4 is the superior fascia surface of the pectoralis major muscle 8. The space 3 between the surfaces 2 and 4 represents the body pocket which is desired to be stably maintained. The surfaces 2 and 4 in continuity are the surfaces which are desired to be stably maintained and prevented from growing together.

Figure 2A:
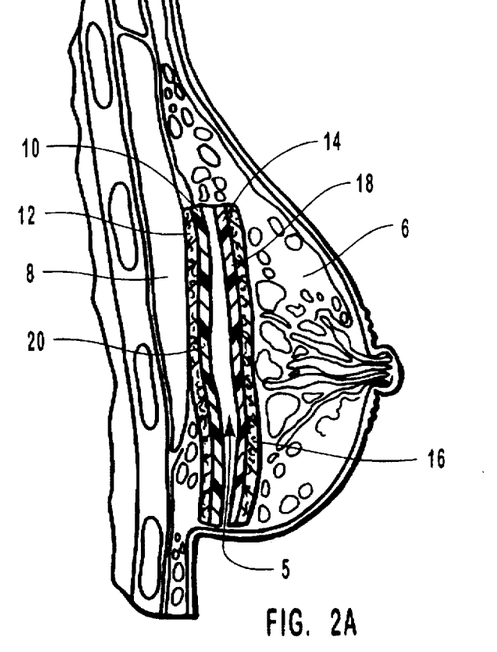
FIG. 2A illustrates an internal cross-section view of a potential space stable body pocket formed by positioning two sheets within a space between tissue surfaces.

In FIG. 2A, it can be seen that each of the two facing tissue surfaces, 2 and 4, is contacted by a sheet in accord with the present invention. Sheet 14 has a tissue-adhering surface 16 placed in contact with the tissue surface 2. Sheet 10 has a tissue-adhering surface 12 placed in contact with tissue surface 4. The architecture of the adhering surfaces is such that tissue ingrowth, fixation and adherence is permitted such that the sheets become stably secured to the respective tissue surfaces. Sheet 14 also has a non-adhering surface 18 and sheet 10 also has a non-adhering surface 20. As illustrated, the sheets may be sized and positioned such that the non-adhering surfaces are facingly aligned with each other and are substantially contiguous. In this manner, a potential space stable body pocket 5 is created between the non-adhering surfaces of the sheets.

The stable body pocket comprises either a potential space or an actual space depending on the shape of the sheets used. Returning to FIG. 2A, it is seen that the sheets conform to the tissue surfaces and substantially directly contact each other such that a potential space stable body pocket is created. An actual space stable body pocket could also be created wherein the sheets are shaped in a manner that maintains a space between the non-adhering sheet surface and a facing surface, either a tissue or sheet surface, such that the surfaces are spaced apart and are not substantially in direct contact with each other. For example, the sheets could be made thicker or semi-rigid or rigid to thereby maintain a desired shape.

Figure 2B:
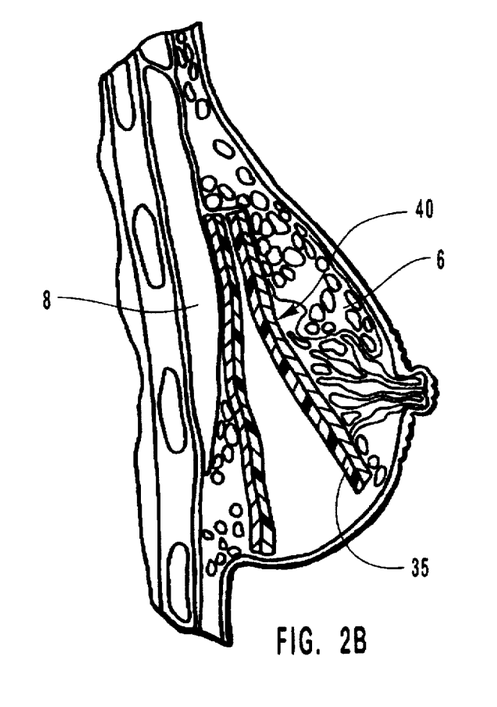
FIG. 2B illustrates an internal cross-section view of an actual space stable body pocket formed by positioning two sheets within a space between tissue surfaces.

Accordingly, as shown in FIG. 2B, sheet 35 could have a rigid or semi-rigid bend designated 40 to thereby create an actual space body pocket having something filling the space. At surgical placement of the sheets, room air and any bleeding or serum which has accumulated and not been removed will partially fill the space. As times goes by after implantation of the sheets, the air will be replaced with serum and/or other extracellular fluids which will be drawn into this space by the pressure generated by the absorption of the air and the resulting negative pressure created within the actual space. Alternatively, the surgeon could fill the space with a desired solution or substance at the time of implantation or thereafter through a needle inserted through the overlying tissue or through a tube placed into the space. For example, desired solutions include normal saline with or without added substances such as antibacterial compounds, or other types of irrigation solutions or pharmaceutical solutions.

Figure 3A:
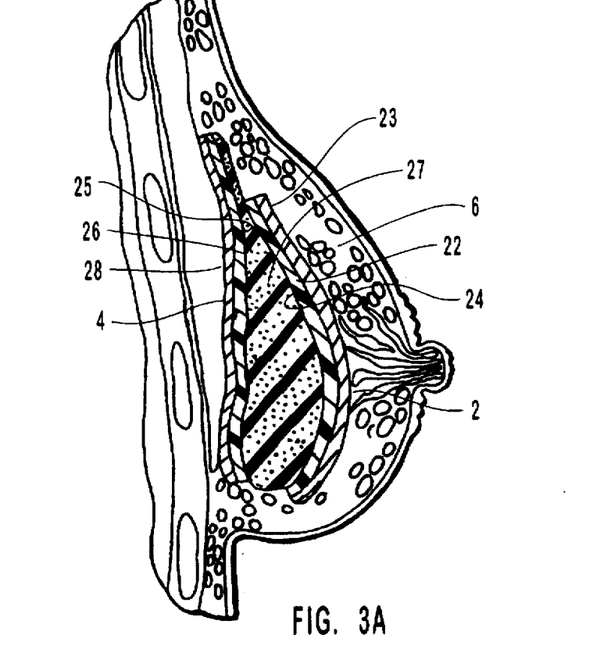
FIG. 3A illustrates an internal cross-section view of a stable body pocket formed by positioning two sheets within a space between tissue surfaces which contains a breast implant.

FIG. 3A illustrates an embodiment of the present invention utilizing two sheets to maintain a stable body pocket for a breast implant. The sheets are positioned within an anterior chest pocket as shown in FIG. 1 and a breast implant 27 is positioned within the stable body pocket space. As shown, one sheet 22 is positioned with the tissue-adhering surface 23 contacting tissue surface 2, the under-surface of the breast gland 6. Another sheet 26 is positioned with the tissue-adhering surface 28 contacting tissue surface 4, the superior fascia surface of the pectoralis major muscle 8. Sheet 22 has a non-adhering surface 24 and sheet 26 has a non-adhering surface 25. The sheets may be sized and shaped to essentially fully line the interior surface of the body pocket, or as shown in FIG. 3A, the sheets may only partially line the body pocket.

The sheets in FIG. 3A are not contiguous with each other. The non-adhering surfaces of the sheets are substantially in contact with the breast implant. Above the implant, it can be seen that a portion of sheet 26 faces the tissue surface above the implant such that the non-adhering surface 25 of sheet 26 may contact the tissue surface in this superior space where the other sheet 22 does not extend above the implant. It should be understood that sheet 22 could also extend above the implant such that the non-adhering surfaces of the two sheets 22 and 26 would face each other above the implant. The sheets do not need to be completely aligned because the non-adhering surface will not adhere to either tissue, an implant surface, or another sheet surface. It should be further understood that multiple sheets of selected sizes and shapes could be strategically positioned to maintain a body pocket of any desired size, shape and surface area. The stably maintained body pocket depicted in FIG. 3A allows the movement of the breast implant surface and volume into the superior space above the implant. Movement into this potential and/or actual space with minimal force imparts a natural look and feel to the implanted breast.

It will also be appreciated that the sheets could alternatively have some or all of the sheet edges connected to each other such that an apparatus having an outside surface and an inside surface is formed. The sheet edges could be completely or partially connected such that the structure would resemble a pouch, an envelope, or a tube. The pouch or tube could be either entirely or only partially closed.

The stable body pocket could be filled with a medical device, fluid, or other desired material or substance or tissue either at the time of placement of the envelope or at a later time. It may be desirable to position a tube from the body pocket to the exterior of the body for subsequent manipulations such as filling, refilling, or monitoring of the body pocket contents. Alternatively, access to the body pocket could be through a needle inserted through the skin and surrounding tissue into the body pocket or through subcutaneously placed ports or domes well-known in the art.

Figure 3B:
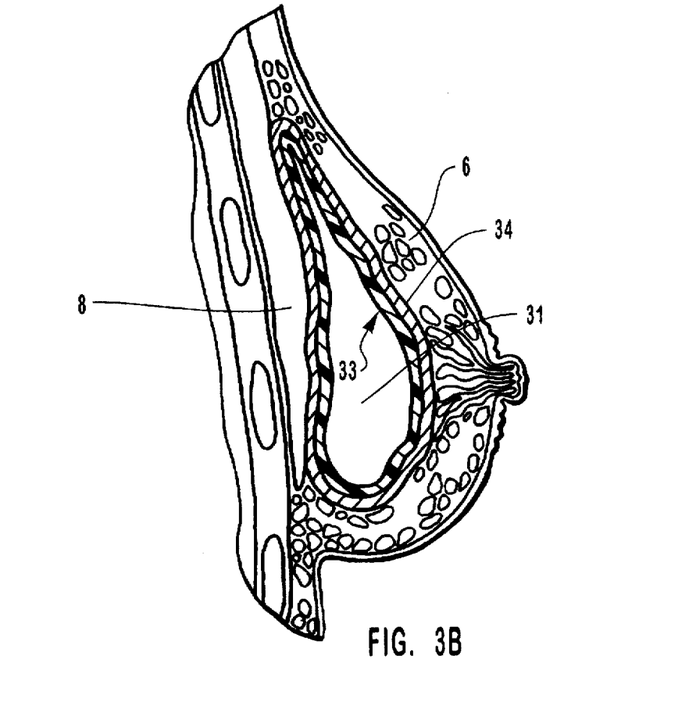
FIG. 3B illustrates an internal cross-section view of a stable body pocket formed by positioning an envelope-shaped sheet between tissue surfaces.

FIG. 3B shows an embodiment wherein the sheets are formed into a closed semi-spherical envelope 31 having an outer tissue-adhering surface 34 and an inner non-adhering surface 33 positioned to fully line the interior tissue surface of an anterior chest body pocket. In this manner, the outer tissue-adhering surface permits tissue ingrowth and creates a stable body pocket. The envelope is filled with fluid, preferably normal saline, at any time prior to the end of the surgery. Alternatively, the fluid could be inserted with a needle or through a tube or subcutaneous port following the surgery as described above. Because the envelope 31 is fixed in position by direct tissue ingrowth, the tissue pocket surface area contacting the envelope outer surface is maintained such that subsequent significant distortion and contracture will not occur. Furthermore, the shape of the surgically created body pocket is completely maintained by the tissue fixation even when the patient stands up.

This is unlike textured breast prostheses currently available which do not actually permit tissue ingrowth. Rather, the textured surface rubs against the tissue surface resulting in formation of a very thick capsule. Because of the lack of actual tissue ingrowth, however, the prosthesis is not securely affixed to the tissue. Thus, the prosthesis will settle into a lower position within the body pocket created at surgery. Once the prosthesis settles, which may occur immediately post-operatively or gradually thereafter, the superior tissue surfaces, i.e., the tissue surfaces above the settled prosthesis, can contact, adhere and heal together. Eventually, the adhered tissue as well as the tissue capsule surrounding the prosthesis contracts causing distortion and increased pressure within the prosthesis. The healing together of the superior tissue surfaces creates a very unnatural and abrupt transition from normal tissue to the tissue surrounding the prosthesis. This also creates an abrupt angle in the skin surface. The thick fibrous capsule contracts into a more spherical shape thereby forcing the breast prosthesis and its contents into a more spherical shape. Even when the patient becomes supine, the shape does not go back to the more natural pancake shape and superior positioning originally created by surgical dissection of the body pocket space, but remains lowered, hard and distorted.

In the above-described embodiments, the sheets are positioned between facing tissue surfaces entirely within a body. It would also be possible, however, to position the sheets between facing tissue surfaces extending to the exterior of the body.

2. Methods and Apparatus for Establishing a Stable Body Pocket Using a Single Sheet of Elastomeric Material Other methods and apparatus for establishing a stable body pocket in accord with the present invention utilize a single sheet of a biocompatible material having a tissue-adhering surface on one side and a non-adherent surface on the other side. As described above with respect to multiple sheets, the single sheet can be positioned within a space, either naturally occurring or surgically created, between facing tissue surfaces within a body. The tissue-adhering surface permits tissue ingrowth and becomes secured to the tissue surface while the non-adhering surface does not adhere to the facing tissue surface. In this manner, a stable internal body pocket can be created.

Figure 4A:
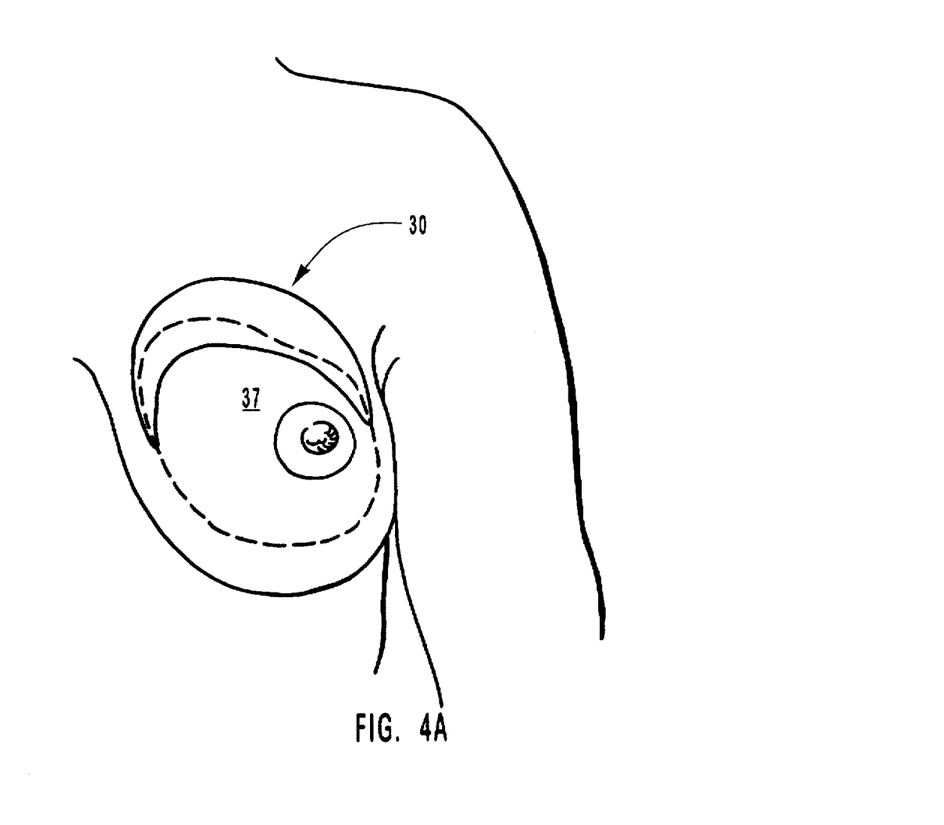
FIG. 4A illustrates schematically a front view of a stable body pocket formed by positioning a single crescent-shaped sheet between tissue surfaces which contains a breast implant.
Figure 4B:
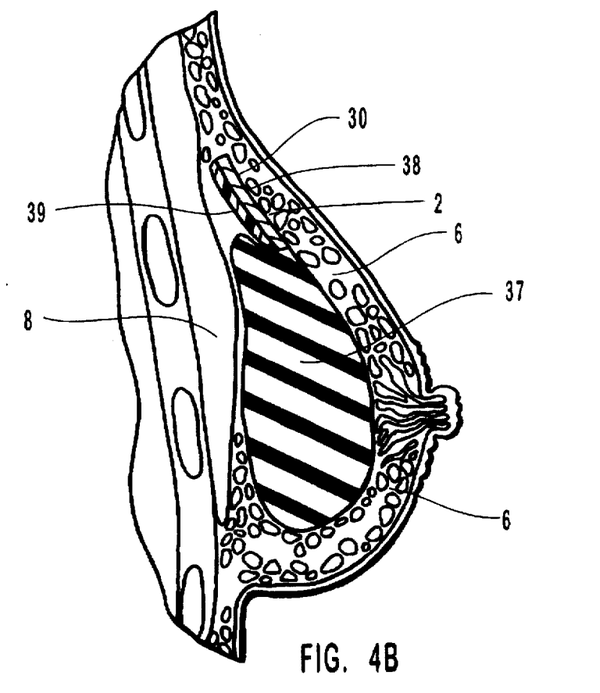
FIG. 4B illustrates an internal cross-section view of the stable body pocket shown in FIG. 4A.

FIGS. 4A and 4B illustrate an alternative embodiment of the present invention utilizing one sheet to maintain a stable body pocket for a breast implant shown in dotted line designated 37. As best seen in FIG. 4A, the sheet 30 is preferably crescent-shaped. As shown in FIG. 4B, the crescent-shaped sheet 30 may be positioned with the tissue-adhering surface 38 contacting a portion of tissue surface 2 such that the non-adhering surface 39 partially contacts the breast implant and partially faces the opposite tissue surface 4. Alternatively, it should be understood that the sheet could also be positioned with the tissue-adhering surface in contact with tissue surface 4 and achieve the same result. In this manner, the tissue surfaces are prevented from contacting each other and healing together. The non-adhering surface 39 of sheet 30 thereby maintains the body pocket such that, when the patient is upright, there is an unfilled potential space stable body pocket superior to the breast implant such that when the patient is supine, or compressed, as by lying on her chest or being hugged, the breast implant can move into the potential space stable body pocket in a natural manner.

Alternatively, the facing tissue surfaces could be surgically created at a body surface and the sheet could be positioned between the facing tissue surfaces with a portion of the sheet extending to outside of the body. It should be understood that the sheet may be sized and shaped in any desired manner to create a body pocket having the desired size and shape. In this manner, a stable body pocket accessible from outside of the body would be created.

In any of these alternative embodiments, the tissue-adhering surface of the sheet is placed in contact with a tissue surface. The tissue-adhering surface permits tissue ingrowth which stably secures the sheet in position. The non-adhering surface of the sheet thus contacts the facing tissue surface. The non-adhering surface, however, does not permit tissue ingrowth and does not adhere to the tissue surface. In this manner, a stable body pocket is created between the non-adhering sheet surface and the facing tissue surface. The stable body pocket comprises a potential space if the non-adhering surface and the tissue surface are substantially in direct contact with each other.

The method and apparatus could also be used to create an actual space stable body pocket. The sheet could be made thicker or semi-rigid or rigid and shaped or positioned such that the tissue surface and non-adhering surface of the sheet are positioned apart from each other, i.e., the non-adhering sheet surface and the tissue surface are prevented from being substantially in direct contact with each other. As described above for stable body pockets created with multiple sheets, either a potential space or actual space stable body pocket created from a single sheet could subsequently be utilized for numerous purposes.

3. Methods and Apparatus for Establishing a Stable Body Pocket Having Flexible Surface Portions Yet another alternative embodiment of the present invention utilizes either a single sheet or multiple sheets, composed of a biocompatible material, each sheet having a smooth or other type of surface on one side, which will not adhere to contacted surfaces. The other side of each sheet is selectively tissue-adhering in that it has portions that are non-adhering and portions which are tissue-adhering, i.e., portions with promote tissue ingrowth. Any of the methods described above for single or multiple sheets, either positioned separately or formed into a pouch or envelope could be used, to create either a potential space or an actual space stable body pocket with the selectively tissue-adhering surfaced sheets. However, because only selected portions of the surface are tissue-adhering, the areas of tissue ingrowth surrounding a body pocket could be selectively controlled according to the quantity and placement of the tissue-adhering surface portions. Consequently, some portions of the sheet surface would be secured to the tissue surface by tissue ingrowth and other portions would remain unadhered such that the sheet surface could flex to some degree. This type of flexible stable body pocket might be suitable for various uses.

For example, the tissue contracture associated with currently used breast prostheses described above in connection with FIG. 3B, also forces the surface of the breast prosthesis to "scallop" or fold upon itself, particularly in the superior portion. This is so because, as the tissue capsule contracts, the inner tissue surface area is reduced thereby forcing the surface area of the prosthesis to fold upon itself. For textured silicone rubber prostheses, the inherent stiffness of the silicone rubber and the increased thickness created by the dimensions of the texturing create an objectionable thickness which is palpable as an edge through the skin and also gives the skin the appearance of an underlying protuberance. This effect is magnified when contracture occurs and creates a three dimensional point as occurs at the intersection of three planes coming together such as in folding a handkerchief. This effect is especially apparent in the thin skin superiorly and superior medially in the breast.

Figure 3C:
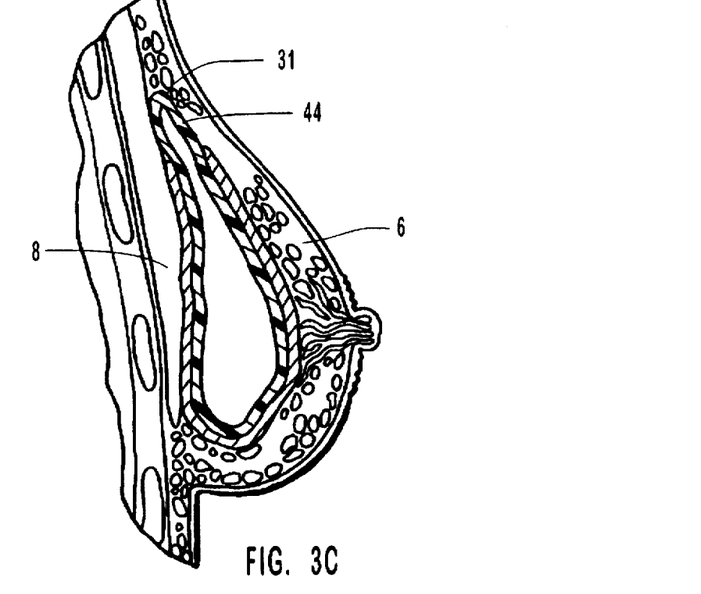
FIG. 3C illustrates an internal cross-section view of an alternative stable body pocket formed by positioning an envelope-shaped sheet between tissue surfaces.

Accordingly, as a further refinement of the present invention, portions of the outer surface of the envelope or pouch shown in FIG. 3B could be made non-adhering and/or thin to control the areas where the surface can fold upon itself. Such an embodiment is shown in FIG. 3C. Due to the increased material and the architectural modification required to make breast implant shells textured, porous or otherwise capable of permitting tissue ingrowth and fixation, stiffness results in the material which does not allow folding back on itself. But some ability for folding back is desirable in response to body movements. Thus, an envelope such as shown in FIG. 3C could be formed having portions of the outer surface which are non-adhering and/or thin at selected locations. As illustrated, a non-adhering outer surface portion 44 on the semi-spherical envelope 31 could be located near the superior portion of the pocket such that the superior edge surface can sharply fold upon itself or scallop in that area and yet not produce visible or palpable edges.

The envelope could be filled with an implant, such as a breast implant, such that the implant would be freely movable within the envelope. Alternatively, the envelope itself could be completely closed and filled with silicone gel, saline, or other suitable substance and used as the implant. The tissue-adhering portions of the outer envelope surface would permit tissue ingrowth and secure the envelope to the surrounding tissue while the non-adhering portions of the outer envelope surface would not adhere to the adjacent tissue surface. In this manner, the non-adhering surface portions would permit a degree of flexing or folding of those portions of the envelope surface within the potential space created between those portions and the adjacent tissue surface. In the case of a breast implant, such flexing or folding of the envelope surface would be advantageous to avoid a wrinkled body surface appearance or unnatural localized areas of firmness, in response to the folding of the enclosed substance, or enclosed implant, such as occurs in response to body movements and positional changes or in response to capsular contracture. Because of the non-adherent outer surface portions, the envelope would have some thin and flexible surface portions.

Figure 6:
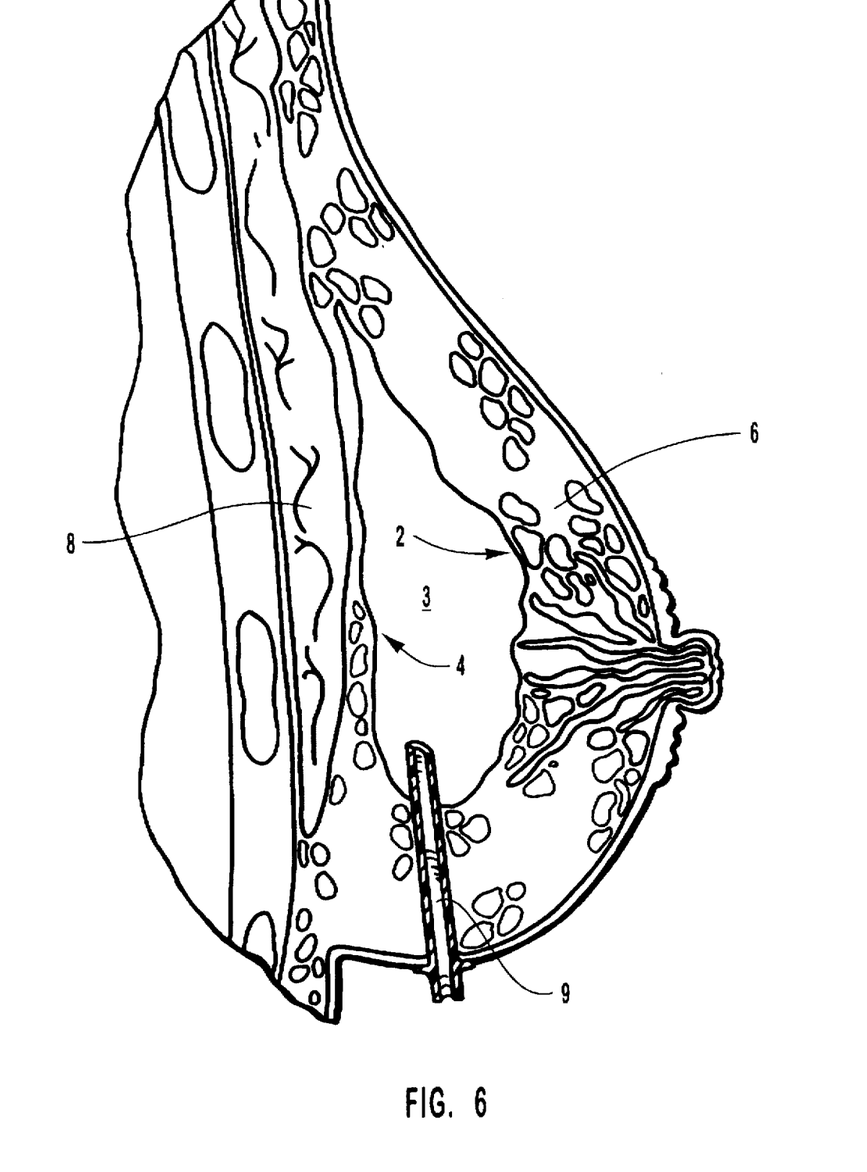
FIG. 6 illustrates a method of forming a stable body pocket.

4. Methods for Establishing and Maintaining a Stable Body Pocket Between Tissue Surfaces An alternative method for establishing and maintaining a stable body pocket between tissue surfaces within a body utilizes the principle of causing a tissue reaction to a foreign material. An access channel, which can be either temporary or permanent, is created to permit pressure from injected fluid or gas to create a stable body pocket at a desired location within either a natural or surgically-created space between facing tissue surfaces. For example, as shown in FIG. 6, the access channel could be simply a tube 9 having one end extending to outside the body through a percutaneous opening and the other end positioned within the space where a body pocket, comprising either a potential space or an actual space, is desired. FIG. 6 depicts a tube 9 positioned within a space surgically created between tissue surfaces, designated 2 and 4, within the anterior chest. The tissue surface 2 is the under-surface of the breast gland 6. The tissue surface 4 is the superior fascia surface of the pectoralis major muscle 8. The space 3 between the surfaces 2 and 4 represents the body pocket which is desired to be stably maintained. The surfaces 2 and 4 in continuity are the surfaces which are desired to be stably maintained and prevented from growing together or contacting during healing.

Injections of fluid, either liquid or gas, may be made through the tube. Alternatively, a filling port or dome of a type known in the art could be implanted with a tube extending to the desired body pocket location. Injections could then be made by inserting a needle into the filling port or dome. It will be understood by those of skill in the art that other methods of access could also be used.

Fluid injected into the space between the facing tissue surfaces causes the tissues to separate. The configuration of the selected natural space or of the surgically-created space, the amount of fluid injected, the pressure of the injected fluid and, in the case of surgical dissection, the location and extent of the dissection, all permit selective control of the size and shape of the resulting body pocket. Moreover, depending on the pressure generated by the injected fluid, either a potential space or an actual space can be established between the facing tissue surfaces. The appropriate pressure is maintained with repeated injections as necessary. The normal reaction of body tissue to contacting a fluid will result in formation of a capsule having a stable surface in approximately 3–14 days in most cases. Thus, maintenance of the appropriate pressure for a sufficient period to resist contracture and prevent tissue contacting and adherence results in establishment of a stable body pocket such that either a potential space or an actual space is created. At this point, the access tube or device could be removed, if desired, and the stable body pocket could be used in any desired manner. It could also be left in position for future injections of fluid or bioactive material, if desired.

It would be possible to form a stable body pocket around an implanted device according to this method. A prosthesis is placed within a surgically-created desired body pocket space having a tube or subcutaneous port. The body pocket space is surgically closed in a water-tight fashion and enough fluid is continuously or intermittently introduced into the space to maintain the body pocket space, during the body pocket maturation period previously described. Care must be taken during healing of the skin incision to not apply too much pressure within the body pocket space and yet apply enough pressure to prevent tissue adherence within the body pocket space. In this manner, a stable body pocket containing a prosthesis is created with only one surgical procedure.

5. Methods and Apparatus for Establishing a Stable Access Channel to a Body Pocket Any of the above-described stable body pockets, or any natural or surgically-created body pocket, can be made stably accessible from the outside of the body through the use of a sheet, or sheets, composed of biocompatible material, in accord with the present invention. The sheet or sheets are positioned to maintain a percutaneous opening and internal access channel in communication with the body pocket site. The sheet or sheets are positioned to permit tissue ingrowth into the surrounding tissue surfaces and thereby become stably secured in position. Insertion and removal of various catheters, syringes, shunts, etc. is thereby accommodated. Injection of fluid into the containment cavity and withdrawal of material from within the body pocket is also facilitated. As described above, stable access channels could be used to connect a device such as an artificial heart to external components.

Figure 5A:
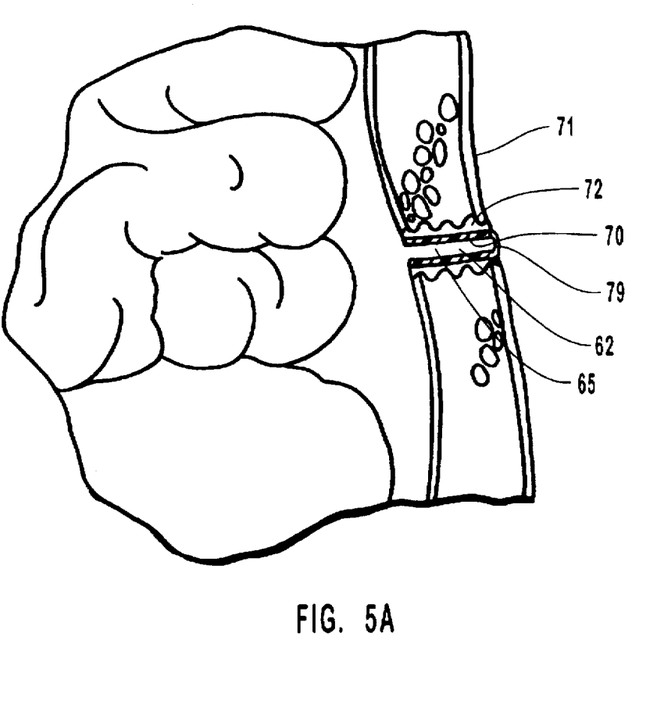
FIG. 5A illustrates a cross-section view of a stable body pocket access channel.

For example, as shown in cross-section in FIG. 5A, either a single sheet or multiple sheets could be formed into a tube 62 having an outer tissue-adhering surface 72 and an inner non-adhering surface 70. Tube 62 could be positioned as illustrated to extend from the exterior surface of the skin 71 through the subcutaneous tissue and the rectus muscle and through the peritoneum to the peritoneal cavity 50. The tissue-adhering surface 72 permits tissue ingrowth and thereby stably secures tube 62 in position. In this manner, a stable body pocket is created providing access to the peritoneal cavity 50 from outside of the body.

Tube 62 defines a stable body pocket extending from the exterior surface of the skin 71 to the interior surface of the peritoneum thereby providing an access channel 65 which connects the peritoneal cavity 50 to the outside environment. The exterior tissue-adhering surface 72 of tube 62 permits tissue ingrowth and thereby becomes securely fixed in place. The natural internal body forces may collapse access channel 65 such that a potential space body pocket is created. Additionally, at the percutaneous opening 79, a cap (not shown) can be placed or an integral valve or port (not shown) can be formed such that addition or removal of fluids or other materials into access channel 65 can be controlled.

Figure 5B:
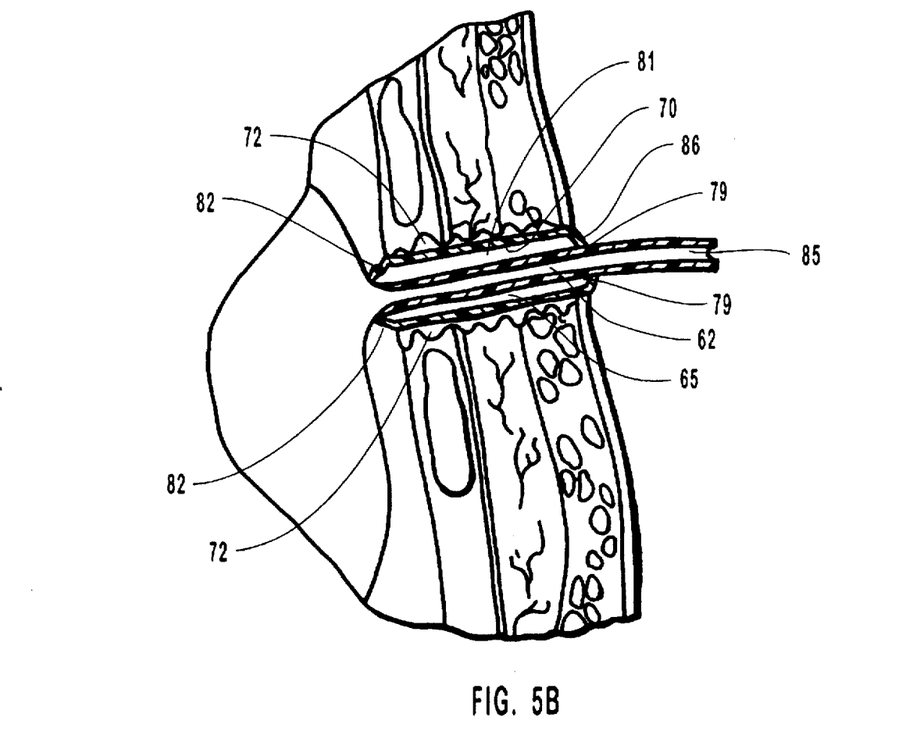
FIG. 5B illustrates a cross-section view of a stable body pocket access channel containing a pressure line.

One use of such a stable body pocket access tube would be to provide access for a heart assist device or an implanted artificial heart. As shown schematically in cross-section in FIG. 5B, a pressure line 85 could be positioned within the stable body pocket access channel 65 shown in FIG. 5A. The pressure line is smaller in diameter than access channel 65 and is sealed to tube 62 around percutaneous opening 79 and around opening 82 into the peritoneal cavity. This sealing creates a cushion space 81 between the outer surface of the pressure line and the inner surface 70 of the tube. An opening 86 to this space provides means for filling the space with fluid, either liquid or gas, or other substances or bioactive material. For example, an antibiotic solution could be placed into the space such that diffusion into the surrounding tissue could occur. The cushion space 81 thereby provides a flexible cushion permitting some movement of the pressure line 85 within tube 62 while still maintaining enough pressure to keep the outer surface 72 of tube 62 in contact with the ingrown surrounding tissue.

Figure 5C:
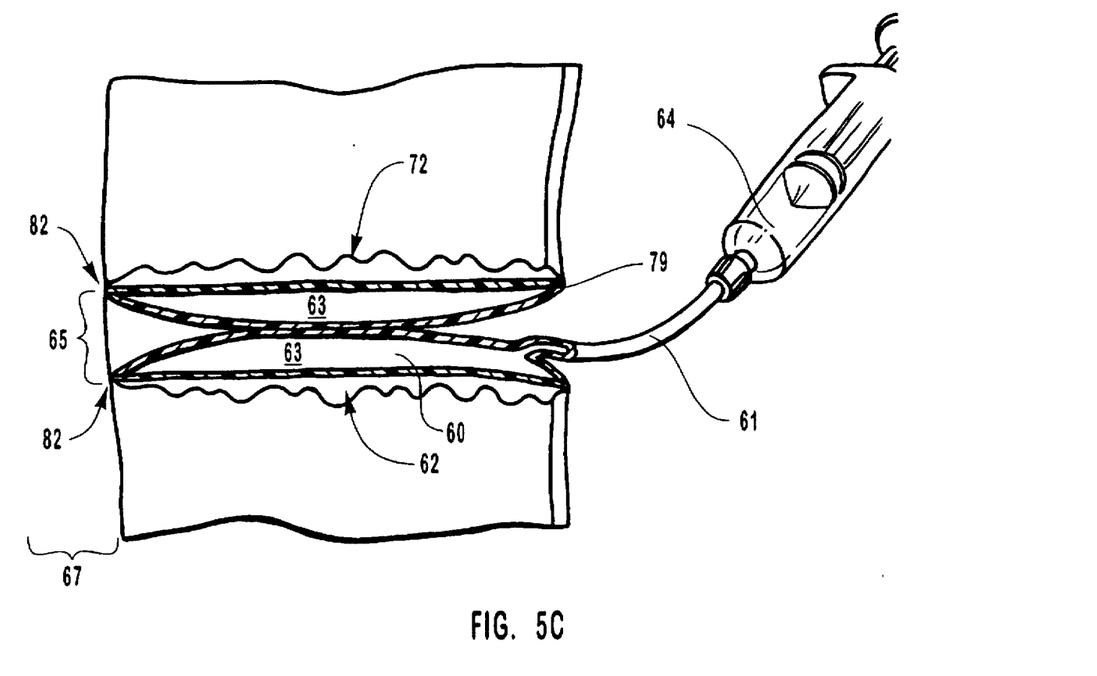
FIG. 5C illustrates a cross-section view of a stable body pocket access channel containing a balloon tube.

A stable body pocket access tube as shown in cross-section in FIG. 5A could also be used to contain a balloon type apparatus to provide control of access through the tube. An example of an embodiment comprising a collapsible balloon tube positioned within the access tube is shown in FIG. 5C. The balloon tube 60 is formed of a flexible biocompatible sheet material having non-adhering surfaces. The balloon tube 60 is of a smaller diameter than tube 62 and is positioned within tube 62. The balloon tube 60 is connected to tube 62 such that a continuous inflatable space 63 is formed between the outer surface of the balloon tube and the inner surface of tube 62. For example, as shown in FIG. 5C, the balloon tube 60 is joined to tube 62 at or near the percutaneous opening 79 and at or near the opening 82 into the peritoneal cavity.

The sheet material for forming the access channel tube and the balloon tube can be any suitable material which can contain the desired fluid, gas or other desired material. The sheet material can be either permeable, semi-permeable, or non-permeable depending on the desired volume of the inflatable space and the desired leakage through the sheets into the tissue ingrowing at the outer surface 72 of tube 62 or into access channel 65 through balloon tube 60. The inflatable space 63 can then be inflated or deflated with a gas, such as nitrogen or carbon dioxide or room air, or a liquid such as normal saline, with or without additives such as antibiotics. Fluid can be added to or withdrawn from the inflatable space 63 either by needle puncture, or by a tube 61, positioned to provide access from outside the body to the inflatable space 63, connected to a syringe 64. In this manner, fine adjustment of the volume within inflatable space 63 can be achieved. Adjustment of the volume within inflatable space 63 controls the opening through tube 62 thereby permitting control of access between the peritoneal space 67 and the outside environment.

It should be understood that the inflatable space could be divided into two or more separate inflatable spaces thereby permitting separate control of volumes within the inflatable spaces at various points along access channel 65. A stable body pocket access channel containing one or more inflatable spaces could be utilized for various purposes.

For example, a stable body pocket access channel containing a balloon tube as shown in FIG. 5C could be used for peritoneal dialysis. The inflatable space is filled with normal saline to an appropriate volume to keep the outside environment from entering the access channel. An antibacterial substance, such as dilute iodophor solution, can be included in the normal saline. The solution can diffuse across the balloon tube membrane in either direction. Specifically, the solution can diffuse into the access channel lumen or into the tissue surrounding the tube to reduce bacterial or bacterial biofilm growth. In this manner, the balloon tube acts as a drug delivery system.

When peritoneal dialysis is desired, the balloon tube is deflated to the desired volume to just allow insertion of a single catheter from the outside of the body to the peritoneal space. Dialysis fluids can then be introduced into the peritoneal space, the catheter removed, and the balloon reinflated. The dialysis fluid, or any other desired fluid such as, for example, solutions of antibiotics, chemotherapeutic agents, or other such bioactive material, is allowed to contact the peritoneal contents for a selected period of time known as the dwell time. The balloon tube can then be partially or totally deflated so that a second catheter can be inserted into the peritoneal cavity to drain the dialysate containing the removed toxins, additional water, or any accumulated substance requiring removal from the peritoneal space. The cycle can be immediately repeated or any desired combination of dialysis fluid, balloon fluid, or catheter introduction or removal can be instituted. In this manner, the need to use flanges, cuffs, or other fixation devices to secure the pocket maintaining device to the skin, peritoneum, muscle or subcutaneous tissue is reduced. However, if desired, a subcutaneous skin cuff and/or a pre-peritoneal or rectus muscle cuff can be formed by extending the tissue-adhering surface of the sheet forming tube 62 such that tissue ingrowth into the surrounding tissue occurs at the desired cuff sites. In this manner, the tube is even more securely fixed in position.

6. A Preferred Surface for Apparatus in Accord with the Present Invention

Various types of surfaces permit tissue ingrowth at a tissue surface interface. The biocompatible sheet material can be an elastomeric material such as silicone rubber, or some other type such as porous polyurethane, expanded polytetrafluroethylene or other such material. The surface architecture which permits tissue ingrowth can comprise a textured, fabric, or porous surface. For example, a foamed silicone porous surface, or sintered or spun porous materials could be used. Fabrics such as dacron felt, velours, or fabric weaves could be used. Textured surfaces such as are formed by salt impregnation and dissolution or are formed by known molding, casting, or flowing procedures to create irregular surfaces could be used.

A preferred surface for use in the practice of the present invention is described in co-pending application Ser. No. 08/156,675 filed Nov. 22, 1993, a continuation of Ser. No. 07/779,387 filed Oct. 18, 1991, now abandoned. The preferred surface comprises an open-cell porous surface that has been discovered to promote tissue ingrowth of a particularly high quality. This "high quality" tissue ingrowth has advantages beyond merely permitting adherence to a tissue surface. The high quality tissue is vascularized and provides a more advantageous environment than the generally poorly vascularized, fibrous tissue ingrowth generated by other types of surface/tissue interfaces.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for use in establishing a stable body pocket within a body, comprising:
    pocket stabilizing means for preventing undesired tissue adherence and for maintaining a stable pocket space capable of accommodating a selected substance or material, said pocket stabilizing means comprising at least one biocompatible sheet, said biocompatible sheet comprising:
        a unitary material of non-biological origin having a first surface on one side thereof which will permit tissue ingrowth to thereby secure the sheet in position to contacted tissue; and
        having a second surface on the other side thereof which will not permit tissue ingrowth or otherwise adhere to contacted surfaces, wherein said biocompatible sheet is positioned between facing tissue surfaces within a body such that said first surface becomes stably secured to at least one of said facing tissue surfaces by said tissue ingrowth and said second surface does not become ingrown with tissue and prevents adherence of the sheet to another surface.

2. A method for establishing a stable body pocket within a body, comprising the steps of:
    obtaining an apparatus having pocket stabilizing means for preventing undesired tissue adherence and for maintaining a stable pocket space capable of accommodating a selected substance or material, said pocket stabilizing means comprising at least one biocompatible sheet comprising a unitary material of non-biological origin and having a first surface on a first side which will ingrow into a contacted tissue surface and a second surface on a second side which will not ingrow into tissue or otherwise adhere to contacted surfaces; and
    positioning said at least one biocompatible sheet between facing tissue surfaces within a body such that the first surface is in contact with a tissue surface at a location where the at least one sheet is desired to be secured by tissue ingrowth; and
    permitting tissue to ingrow into the first surface of the at least one biocompatible sheet so as to secure the sheet in place, and thereby forming a stable body pocket between the second surface of said sheet and a facing surface.

3. An apparatus for use in establishing a stable body pocket within a body as described in claim 1 wherein the at least one sheet is flexible to conform to the body pocket contours.

4. An apparatus for use in establishing a stable body pocket within a body as described in claim 1 wherein the at least one sheet is fixed in a selected shaped configuration.

5. An apparatus for use in establishing a stable body pocket within a body as described in claim 1 wherein the at least one sheet is selectively sized and shaped such that the sheet will partially line the interior surface of a selected body pocket.

6. An apparatus for use in establishing a stable body pocket within a body as described in claim 1 wherein the at least one sheet is selectively sized and shaped such that the sheet will substantially fully line the interior surface of a selected body pocket.

7. An apparatus for use in establishing a stable body pocket within a body as described in claim 1 wherein the surface of the sheet which will permit tissue ingrowth further comprises non-adhering surface portions which will not adhere to contacted surfaces such that the surface of the sheet is capable of folding upon itself at said non-adhering portions.

8. An apparatus for use in establishing a stable body pocket within a body as described in claim 1 wherein the surface of the sheet which will permit tissue ingrowth further comprises thin surface portions such that the surface of the sheet is capable of folding upon itself at said thin portions.

9. An apparatus for use in establishing a stable body pocket within a body as described in claim 1 wherein the surface of the sheet which will permit tissue ingrowth further comprises an open-cell porous surface.

* * * * *